United States Patent [19]

Chorvat

[11] 4,205,004
[45] May 27, 1980

[54] 25-ALKYLCHOLEST-5-ENE-3β,22-DIOLS AND ESTERS THEREOF

[75] Inventor: Robert J. Chorvat, Arlington Heights, Ill.

[73] Assignee: D. G. Searle & Co., Skokie, Ill.

[21] Appl. No.: 929,068

[22] Filed: Jul. 28, 1978

Related U.S. Application Data

[63] Continuation-in-part of Ser. No. 828,385, Aug. 29, 1977.

[51] Int. Cl.² ................................................. C07J 9/00
[52] U.S. Cl. .................................................. 260/397.2
[58] Field of Search .................................... 260/397.2; /Machine Searched Steroids

[56] References Cited

U.S. PATENT DOCUMENTS 4,006,172  2/1977  Salmond ............................ 260/397.2

OTHER PUBLICATIONS

J. Biol. Chem. (1974) No. 249, Article by Kandutsch et al., pp. 6057, etc.
J. Chem. Res. (1977) Article by Nagana et al., pp. 2522, etc.
Md. Cryst. Lig. Cryst. (1971) p. 255, Article by Elser et al.
J. Biol. Chem. (1974) 249, Article by Brown et al., pp. 7306 etc.
C.A. vol. 85 (1976) Pars. 91,024(e).

*Primary Examiner*—Elbert L. Roberts
*Attorney, Agent, or Firm*—John M. Brown; James R. Henes; Albert Tockman

[57] ABSTRACT

25-Alkylcholest-5-ene-3β,22-diols and esters thereof adapted to inhibit the activity of 3-hydroxy-3-methylglutaryl coenzyme A reductase are disclosed.

3 Claims, No Drawings

25-ALKYLCHOLEST-5-ENE-3β,22-DIOLS AND ESTERS THEREOF

The application for Letters Patent securing the invention herein described and claimed is a continuation-in-part of the applicant's copending application, Ser. No. 828,385 filed Aug. 29, 1977.

This invention relates to 25-alkylcholest-5-ene-3β,22-diols and esters thereof. More particularly, this invention relates to new, useful, and unobvious chemical compounds of the formula

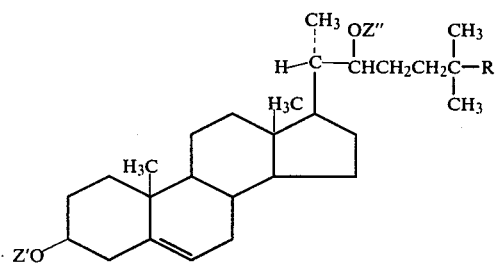

wherein R represents alkyl and Z' and Z" each represent hydrogen or an esterifying moiety such as 1-oxoalkyl frequently but not invariably Ω-substituted by carboxyl.

Among the alkyls represented by R, those containing fewer than 5 carbons are preferred, namely, methyl, ethyl, 1-methylethyl, 1,1-dimethylethyl, propyl, 1-methylpropyl, 2-methylpropyl, and butyl.

Among the esterifying moieties represented by Z' and Z", those of the formula

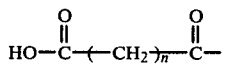

wherein n represents a positive integer less than 4 are preferred, namely, 2-carboxy-1-oxoethyl, 3-carboxy-1-oxopropyl, and 4-carboxy-1-oxobutyl.

The compounds to which this invention relates are useful by reason of their valuable pharmacological properties. Thus, for example, they inhibit the activity of 3-hydroxy-3-methylglutaryl coenzyme A (HMG CoA) reductase, an enzyme which controls the rate at which cholesterol is synthesized in mammalian liver (one of the two principal sources of serum cholesterol). The innovative significance of compounds adapted to inhibit sterol biosynthesis in individuals predisposed to familial type II hypercholesterolemia (WHO classification) is widely recognized. See, for example, Breslow et al., Biochem. et Biophys. Acta, 398, 10 (1975); Betteridge et al., Brit. Med. J., 4, 500 (1975); and Brown et al., J. Biol Chem., 249, 7306 (1974).

The HMG CoA reductase-inhibiting activity of the instant compounds can be demonstrated via the following standardized test procedure: Male Charles River CD rats, initially weighing 180–250 g apiece, are randomized in groups of 6, housed in a reverse light cycle (12:12) room, and maintained therein on a standard rat diet plus water ad libitum. To each animal in a group, after at least 3 but not more than 6 days, 5 mg/kg of 20,25-diazacholesterol dissolved in 0.2 ml of physiological saline containing 0.1% of polyoxyethylene sorbitan monooleate (Tween 80) is intragastrically administered on each of 7 consecutive days, during the last 4 of which test compound is concurrently and identically administered at a pre-selected daily dose (commonly 5 mg/kg intragastrically). Controls are provided by a second group of animals identically treated except that test compound is omitted. Within 2–4 hr after treatment is completed, and 5–7 hr into the dark cycle, the animals are anesthetized with 1,1'-oxybisethane and thereupon killed. Livers are quickly removed, washed with a chilled homogenization medium (preparable by dissolving 102.7 g of sucrose, 3.8 g of sodium edetate, and 0.8 g of dithiothreitol in water q.s. 1000 ml), blotted dry, weighed, and homogenized (using 2 ml of the aforesaid chilled medium for each g of liver). The homogenates are centrifuged at 4° C. and 15,000× g for 15 min., whereupon the supernatants are separated and centrifuged at 4° C. and 100,000× g for 60 min. the resultant supernatants are discarded and the residues suspended in half the volume of homogenization medium previously employed (i.e., 1 ml for each g of residue). HMG CoA reductase activity is assayed substantially in accordance with procedures described by L. W. White et al. in Biochemistry, 9, 2713 (1970); M.S. Brown et al. in J. Biol. Chem., 248, 4731 (1973); and P.A. Edwards et al. in Biochim. Biophys. Acta, 409, 39 (1975). Protein is determined by the method of O.H. Lowry et al., J. Biol. Chem., 193, 265 (1951). The data obtained are converted to specific activity (nmol/20 min./mg) for each animal, from which group mean(s) and percent change, relative to controls, are calculated. A statistically significant response ($P \leq 0.05$) is the criterion for HMG CoA reductase inhibition/stimulation.

One of the preferred embodiments of this invention, 25-methylcholest-5-ene-3β,22-diol, was found to inhibit HMG CoA reductase activity in the foregoing test by 51, 27, 18, and 12% at 50, 30, 10, and 5 mg/kg, respectively, and to stimulate such activity by 30% at 1 mg/kg when administered intragastrically as hereinbefore described. The inhibitory activity in the 5–30 mg/kg dosage range is the more remarkable because cholest-5-ene-3β,22-diol stimulated HMG CoA reductase activity by 24% at 30 mg/kg administered intragastrically under the same conditions.

The distinguishing response to 25-methylcholest-5-ene-3β,22-diol in rats set forth above is of course intended merely to illustrate this aspect of the instant invention, and accordingly is not to be construed as either delimiting or exclusionary.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences," 14 Ed., Merck Publishing Company, Eaton, Pa., 1965.

Appropriate dosages, in any given instance, of course depend upon the nature and severity of the condition treated, the route of administration, and the species of mammal involved, including its size and any individual idiosyncrasies which obtain.

Preparation of compounds of this invention proceeds variously as follows: 3α,5-Cyclo-6β-methoxy-23,24-dinor-5α-cholan-20-al [Steroids, 15, 113 (1970)] is contacted in cold tetrahydrofuran under nitrogen with a Grignard reagent of the formula

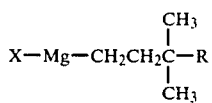   I in which X represents chlorine or bromine, whereupon aqueous ammonium chloride is added to the mixture. The resultant i-steroid alcohol, of the formula

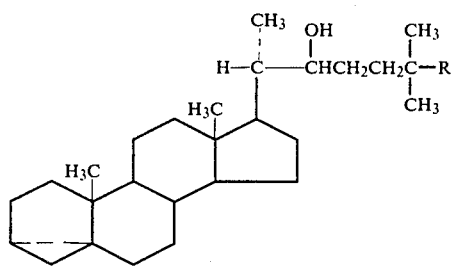   II is rearranged by heating in aqueous dioxane with an acid such as 4-methylbenzenesulfonic acid monohydrate, giving rise to a diol of the invention, having the formula

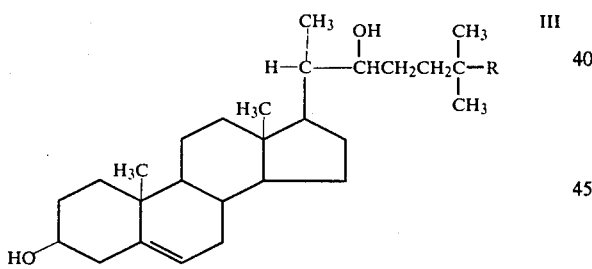   III

Heating a compound of formula II with an alkanoic acid affords a 3-ester of the invention having the formula

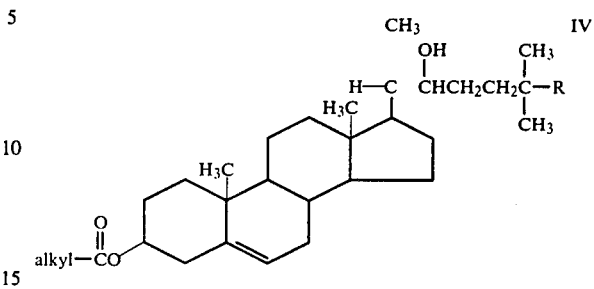   IV whereas heating a compound of formula III in pyridine with an alkanoic acid anhydride or chloride affords a mixture of esters of the invention having the formulas

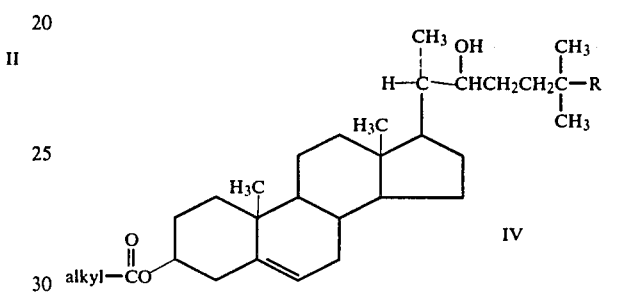   IV

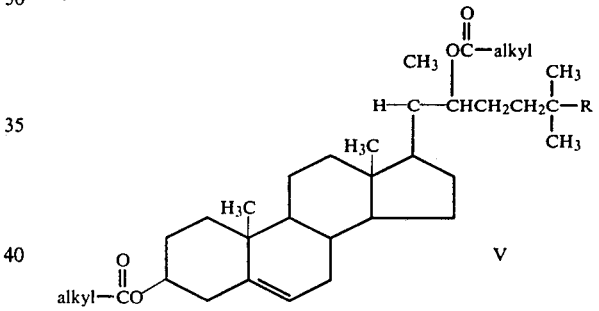   V separable via chromatography on silica gel, using methylbenzene and mixtures thereof with increasing amounts of ethyl acetate as developing solvents. Similarly, heating a compound of formula III in pyridine with a methyl Ω-chloro-Ω-oxoalkanoate affords a mixture of mixed esters having the formulas

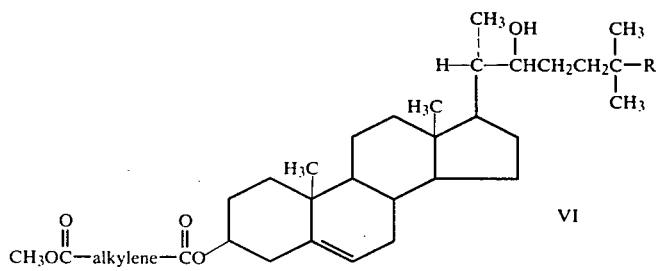   VI

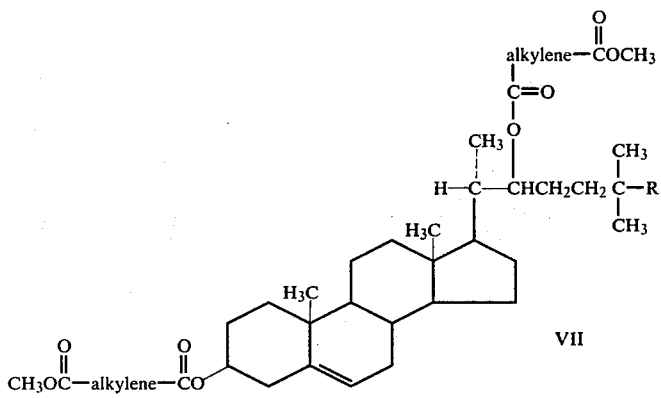

VII separable via chromatography on silica gel as aforesaid; and heating an ester of formula VI or VII with lithium iodide in pyridine, 2,6-dimethylpyridine, or 2,4,6-trimethylpyridine affords an ester of the invention having the formula

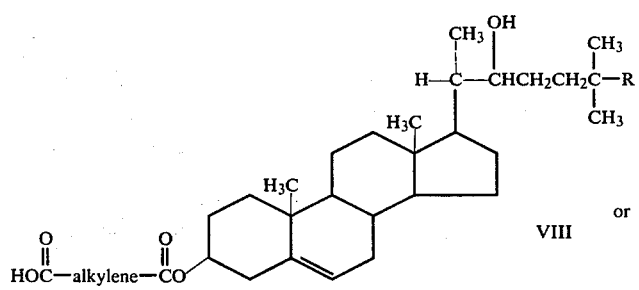

VIII or

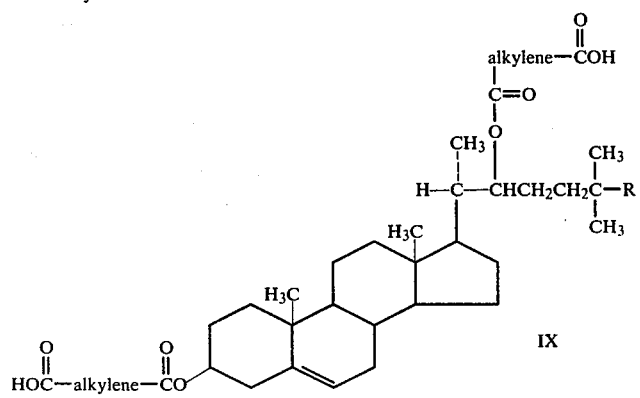

IX respectively. Heating a compound of formula V or IX with sodium bicarbonate in aqueous ethanol affords a 22-ester of the invention having the formula

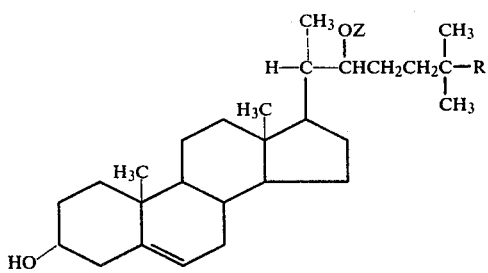

X wherein Z represents 1-oxoalkyl or Ω-carboxy-1-oxoalkyl, respectively. Finally, heating a compound of formula VIII in pyridine with an alkanoic acid anhydride or chloride affords a mixed ester of the invention having the formula

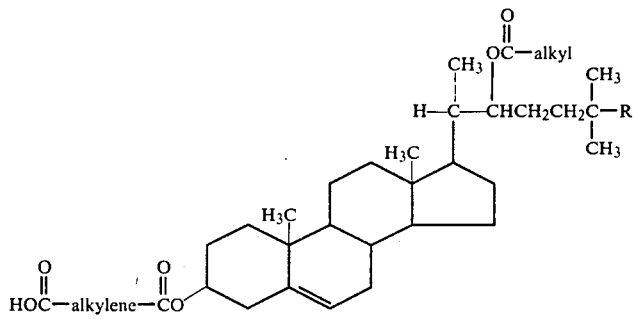

XI

As an exception to the forgoing procedure, a compound of formula VIII wherein the esterifying moiety is 3-carboxy-1-oxopropyl is preferably prepared by heating a compound of formula III with butanedioic acid anhydride in pyridine. In each of formulas I through XI hereinbefore, R represents alkyl preferably containing fewer than 5 carbons.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of approximately 40 parts of 3α,5-cyclo-6β-methoxy-23,24-dinor-5α-cholan-20-al [Steroids, 15, 113 (1970)] in 265 parts of tetrahydrofuran at 0°–5° in a nitrogen atmosphere is slowly added a solution of approximately 17 parts of chloro(3,3-dimethylbutyl)magnesium in 110 parts of 1,1'-oxybisethane. The resultant mixture is stirred at room temperature for 1 hour, then partitioned between an aqueous saturated solution of ammonium chloride and 1,1'-oxybisethane. The 1,1'-oxybisethane phase is separated, washed with an aqueous saturated solution of sodium chloride, dried over anhydrous sodium sulfate, and stripped of solvent by vacuum distillation. The residual oil is 3α,5-cyclo-6β-methoxy-25-methyl-5α-cholestan-22-ol.

B. To a solution of 25 parts of 3α,5-cyclo-6β-methoxy-25-methyl-5α-cholestan-22-ol in 600 parts of 1,4-dioxane and 200 parts of water is added 1 part of 4-methylbenzenesulfonic acid monohydrate. The resultant mixture is heated at 90°–85° for 5 hours, whereupon an equal volume of water is added and the mixture thus obtained is extracted with 1,1'-oxybisethane. The extract is washed with an aqueous saturated solution of sodium chloride, dried over anhydrous sodium sulfate, and stripped of solvent by vacuum distillation. The residual oil, upon trituration with a small amount of ethanol, crystallizes. The crystalline material is filtered off and recrystallized from aqueous ethanol to give 25-methylcholest-5-ene-3β,22-diol, melting at 191°–193°, and having the formula

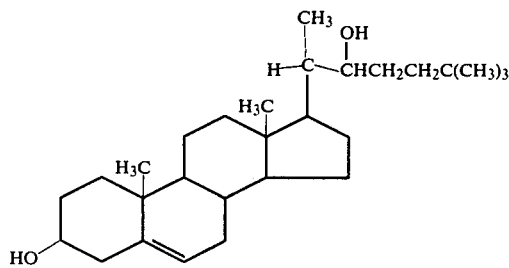

EXAMPLE 2

A mixture of approximately 17 parts of 3α,5-cyclo-6β-methoxy-25-methyl-5α-cholestan-22-ol and 75 parts of glacial acetic acid is heated at 90°–95° for 3 hours, then cooled and thereupon diluted with 300 parts of water. The oily solid which forms is extracted with 1,1'-oxybisethane. The extract is washed with aqueous 5% sodium bicarbonate until the washings remain basic, then dried over anhydrous sodium sulfate and thereupon stripped of solvent by vacuum distillation. The residue is recrystallized from 2-propanone to give 25-methylcholest-5-ene-3β,22-diol 3-acetate melting at 185°–187°, and having the formula

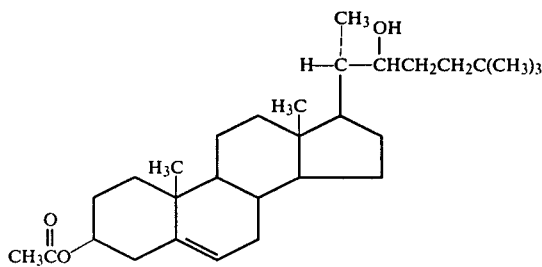

EXAMPLE 3

To a solution of 4 parts 25-methylcholest-5-ene-3β,22-diol in 25 parts of pyridine is added a solution of 1 part of acetyl chloride in 5 parts of pyridine. The resultant mixture is stirred at room temperatures for 6 hours, then diluted with an equal volume of water. The mixture thus obtained is extracted with 1,1'-oxybisethane. The extract is consecutively washed with 5% hydrochloric acid and water, then stripped of solvent by vacuum distillation. The residue is taken up in methylbenzene; and the methylbenzene solution is chromatographed on silica gel, using methylbenzene and mixtures thereof with increasing amounts of ethyl acetate as developing solvents. From eluates selected via thin layer chromatography and stripped of solvent by vacuum distillation, 25-methylcholest-5-ene-3β,22-diol 3-acetate and 25-methylcholest-5-ene-3β,22-diol 3,22-diacetate are isolated as residues which, recrystallized from ethanol, melt at 185°–187° and 175°–177° respectively. (The diester, being the less polar, is eluted first.) The products have the formulas bis(3-methoxy-3-oxopropanoate) are isolated as the residues. (The diester, being the less polar, is eluted first.)

B. A mixture of 4 parts of 25-methylcholest-5-ene-3β,22-diol 3,22-bis(3-methoxy-3-oxopropanoate), 12 parts of lithium iodide, and 30 parts of 2,6-dimethylpyridine is heated at the boiling point under reflux with stirring overnight, whereupon an equal volume of water is added and the solid precipitate which eventuates is filtered off, washed with water, and dried in air. The product thus isolated is 25-methylcholest-5-ene-3β,22-diol 3-(hydrogen propanedioate), having the formula

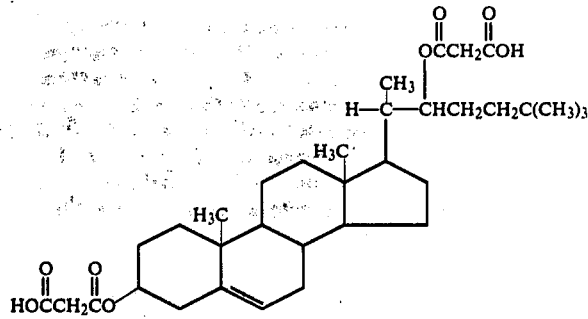

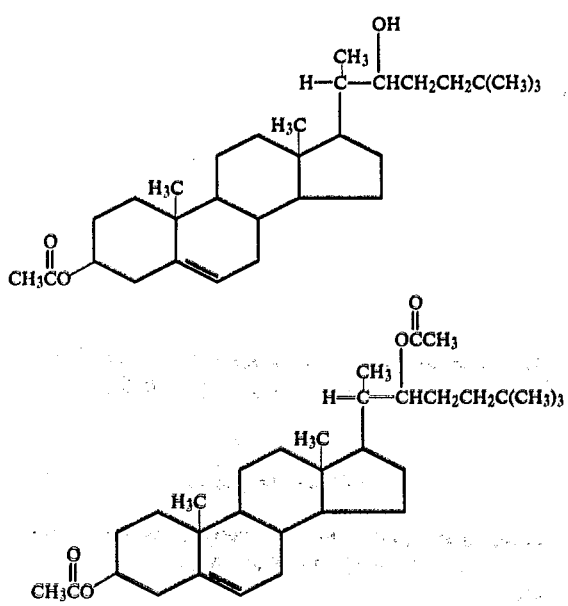

EXAMPLE 5

To a solution of 1 part of 25-methylcholest-5-ene-3β,22-diol 3,22-diacetate in 40 parts of ethanol is added 5 parts of aqueous 5% sodium bicarbonate. The resultant mixture is heated and stirred at the boiling point under reflux for 2½ hours, then diluted with an equal volume of water. The solid precipitate which eventuates is isolated by filtration, dried in air, and recrystallized from ethanol to give 25-methylcholest-5-ene-3β,22-diol 22-acetate melting at 210°–211.5°. The product has the formula

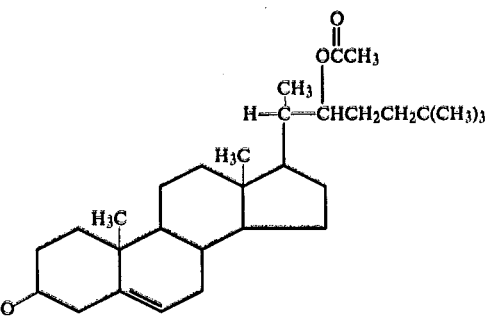

EXAMPLE 4

A. To a solution of 4 parts of 25-methylcholest-5-ene-3β,22-diol in 25 parts of pyridine is added a solution of 2 parts of 3-methoxy-3-oxopropanoyl chloride in 5 parts of pyridine. The resultant mixture is stirred at 90°–95° for 3 hours, then diluted with an equal volume of water. The mixture thus obtained is extracted with 1,1'-oxybisethane; and the extract is consecutively washed with 5% hydrochloric acid and water, then stripped of solvent by vacuum distillation. The residue is taken up in methylbenzene; and the methylbenzene solution chromatographed on silica gel, using methylbenzene and mixtures thereof with increasing amounts of ethyl acetate as developing solvents. From eluates selected via thin layer chromatography and stripped of solvent by vacuum distillation, 25-methylcholest-5-ene-3β,22-diol 3-(3-methoxy-3-oxopropanoate) and 3,22-

EXAMPLE 6

To a solution of 16 parts of 25-methylcholest-5-ene-3β,22-diol in 250 parts of pyridine is added 10 parts of butanedioic acid anhydride. The resultant mixture is heated at 90°–95° for 18 hours, then cooled and thereupon diluted with an equal volume of water. The oil which separates solidifies on stirring. The solid is filtered off and consecutively recrystallized from aqueous ethanol and a mixture of ethyl acetate with hexane to give 25-methylcholest-5-ene-3β,22-diol 3-(hydrogen butanedioate) melting at 190°–193°, and having the formula

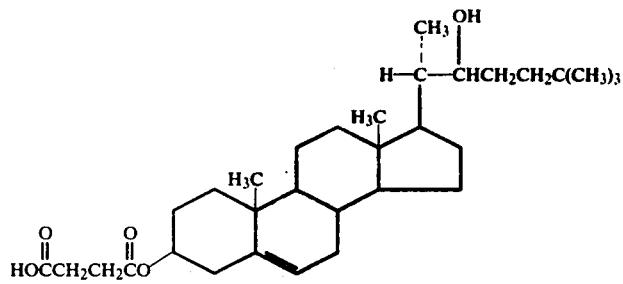

EXAMPLE 7

A mixture of 1 part of 25-methylcholest-5-ene-3β,22-diol 3-(hydrogen butanedioate), 10 parts of pyridine, and 5 parts of acetic anhydride is stirred at room temperatures overnight, then diluted with an equal volume of water. The solid precipitate which eventuates is filtered off, washed with water, and dried in air. The product thus isolated is 25-methylcholest-5-ene-3β,22-diol 22-acetate 3-(hydrogen butanedioate), having the formula

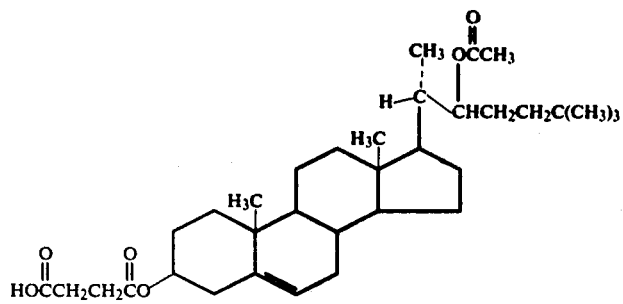

What is claimed is:

1. A compound of the formula

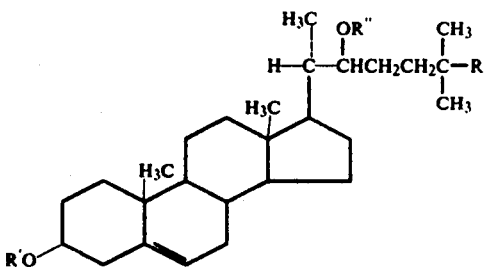

wherein R represents alkyl containing fewer than 5 carbons; R' represents a radical of the formula

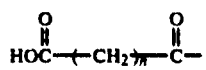

wherein n represents a positive integer less than 4; and R" represents hydrogen, acetyl, or a radical of the formula $$HOC-(CH_2)_n-C-$$

wherein n is defined as before.

2. A compound according to claim 1 which is 25-methylcholest-5-ene-3β,22-diol 3-(hydrogen butanedioate).

3. A compound according to claim 1 which is 25-methylcholest-5-ene-3β,22-diol 3-(hydrogen propanedioate).